(12) United States Patent
Pisharodi

(10) Patent No.: US 10,342,663 B2
(45) Date of Patent: Jul. 9, 2019

(54) DISC AND VERTEBRAL DEFECT PACKING TAPE

(71) Applicant: Perumala Corporation, Brownsville, TX (US)

(72) Inventor: Madhavan Pisharodi, Brownsville, TX (US)

(73) Assignee: Perumala Corporation, Brownsville, TX (US)

( * ) Notice: Subject to any disclaimer, the term of this patent is extended or adjusted under 35 U.S.C. 154(b) by 0 days.

(21) Appl. No.: 15/982,661

(22) Filed: May 17, 2018

(65) Prior Publication Data

US 2018/0263780 A1 Sep. 20, 2018

Related U.S. Application Data

(63) Continuation-in-part of application No. 15/384,301, filed on Dec. 19, 2016, now Pat. No. 9,974,655.

(51) Int. Cl.
| A61F 2/44 | (2006.01) |
| A61F 2/46 | (2006.01) |
| A61F 2/28 | (2006.01) |
| A61F 2/30 | (2006.01) |

(52) U.S. Cl.
CPC .......... *A61F 2/2846* (2013.01); *A61F 2/4611* (2013.01); *A61F 2002/2835* (2013.01); *A61F 2002/30563* (2013.01); *A61F 2002/4435* (2013.01); *A61F 2230/0091* (2013.01)

(58) Field of Classification Search
CPC ..... A61F 2/4415; A61F 2/4455; A61F 2/4611
See application file for complete search history.

(56) References Cited

U.S. PATENT DOCUMENTS

| 5,702,454 | A | 12/1997 | Bumgartner |
| 5,755,797 | A | 5/1998 | Bumgartner |
| 5,919,235 | A | 7/1999 | Husson |
| 6,893,464 | B2 | 5/2005 | Kiester |
| 8,518,118 | B2 | 8/2013 | Sack et al. |
| 2004/0249464 | A1 | 12/2004 | Bindseil et al. |
| 2005/0278023 | A1* | 12/2005 | Zwirkoski .......... A61B 17/7094 623/11.11 |
| 2007/0150064 | A1* | 6/2007 | Ruberte ............... A61F 2/442 623/17.16 |
| 2007/0162132 | A1 | 7/2007 | Messerli |
| 2009/0012622 | A1 | 1/2009 | James et al. |
| 2009/0088799 | A1 | 4/2009 | Yeh |
| 2010/0030241 | A1 | 2/2010 | Yeung et al. |
| 2011/0054408 | A1 | 3/2011 | Wei |

(Continued)

OTHER PUBLICATIONS

USPTO Office Action dated Jun. 12, 2017 issued for parent U.S. Appl. No. 15/384,301.

*Primary Examiner* — Julianna N Harvey
(74) *Attorney, Agent, or Firm* — D'Ambrosio & Menon, PLLC; Usha Menon

(57) ABSTRACT

Embodiments of the invention include a disc or vertebral defect packing tape for use in disc fusion, disc regeneration or for the creation of artificial disks. The tape comprises a tape body and one or more support members. Each of the support members is contained within the tape body and/or adhered to an external surface of the tape or tape body. The tape body is configured as a packing material and each of the support members is configured to hold the tape body together.

6 Claims, 13 Drawing Sheets

(56) References Cited

U.S. PATENT DOCUMENTS

2013/0289599 A1   10/2013  Yeung
2016/0015521 A1*  1/2016  Serrahima Tornel ... A61F 2/442
                                                  623/17.16

* cited by examiner

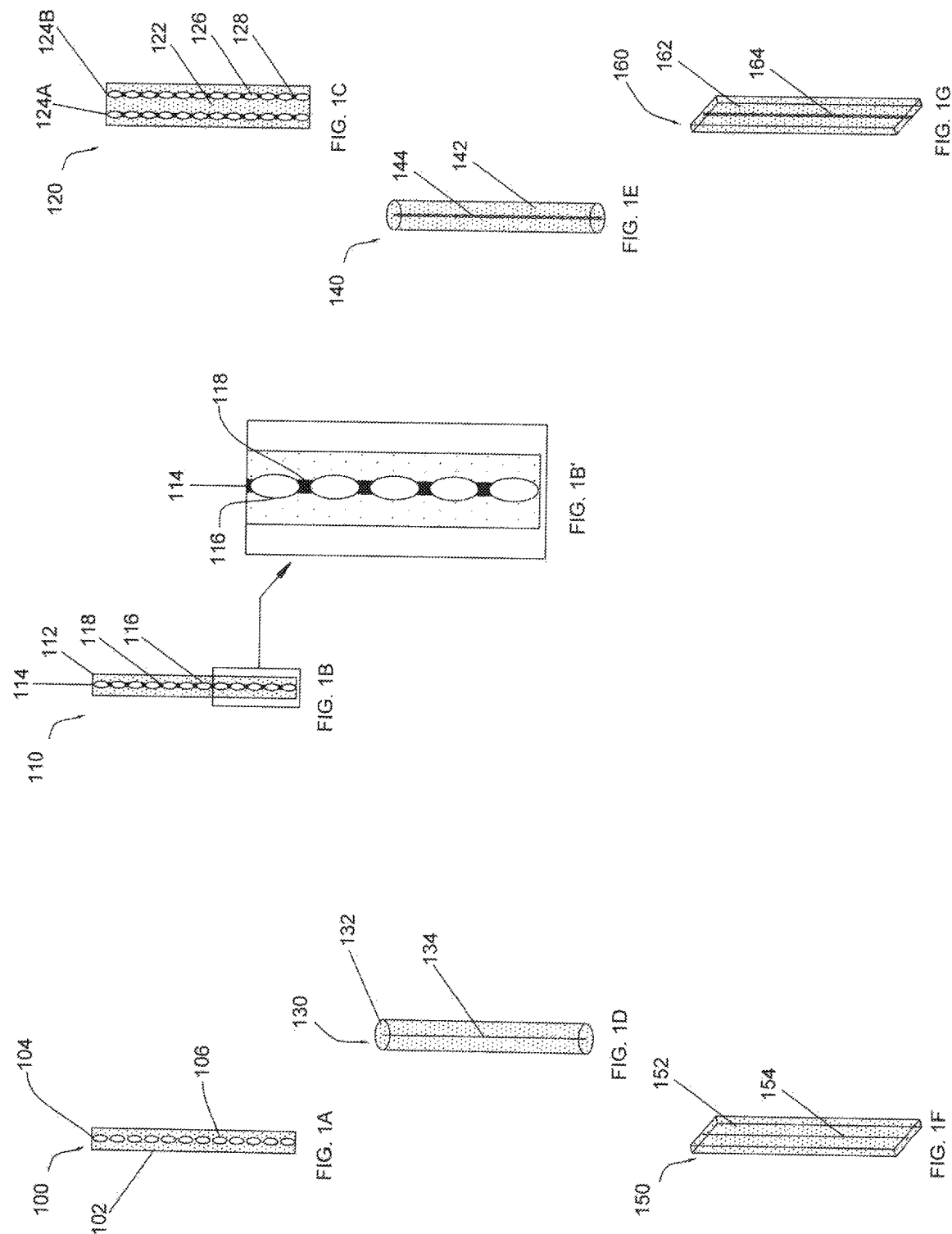

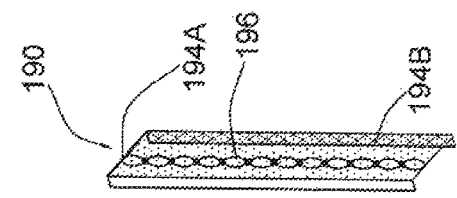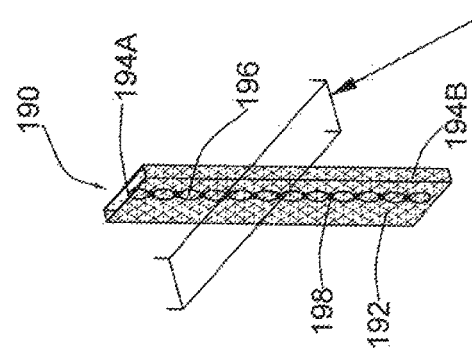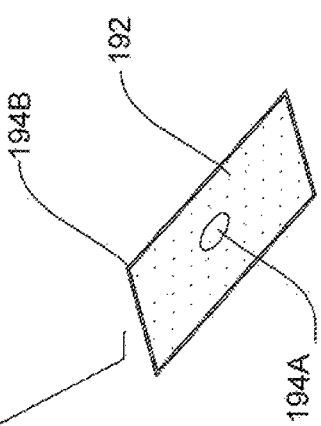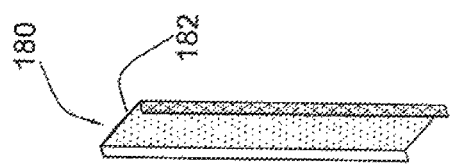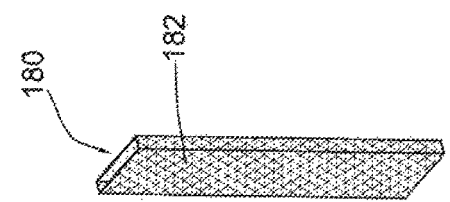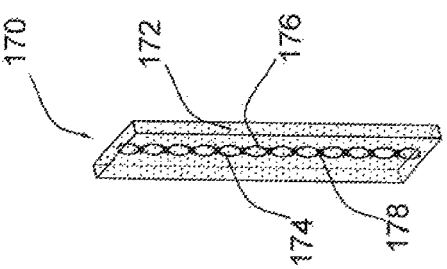

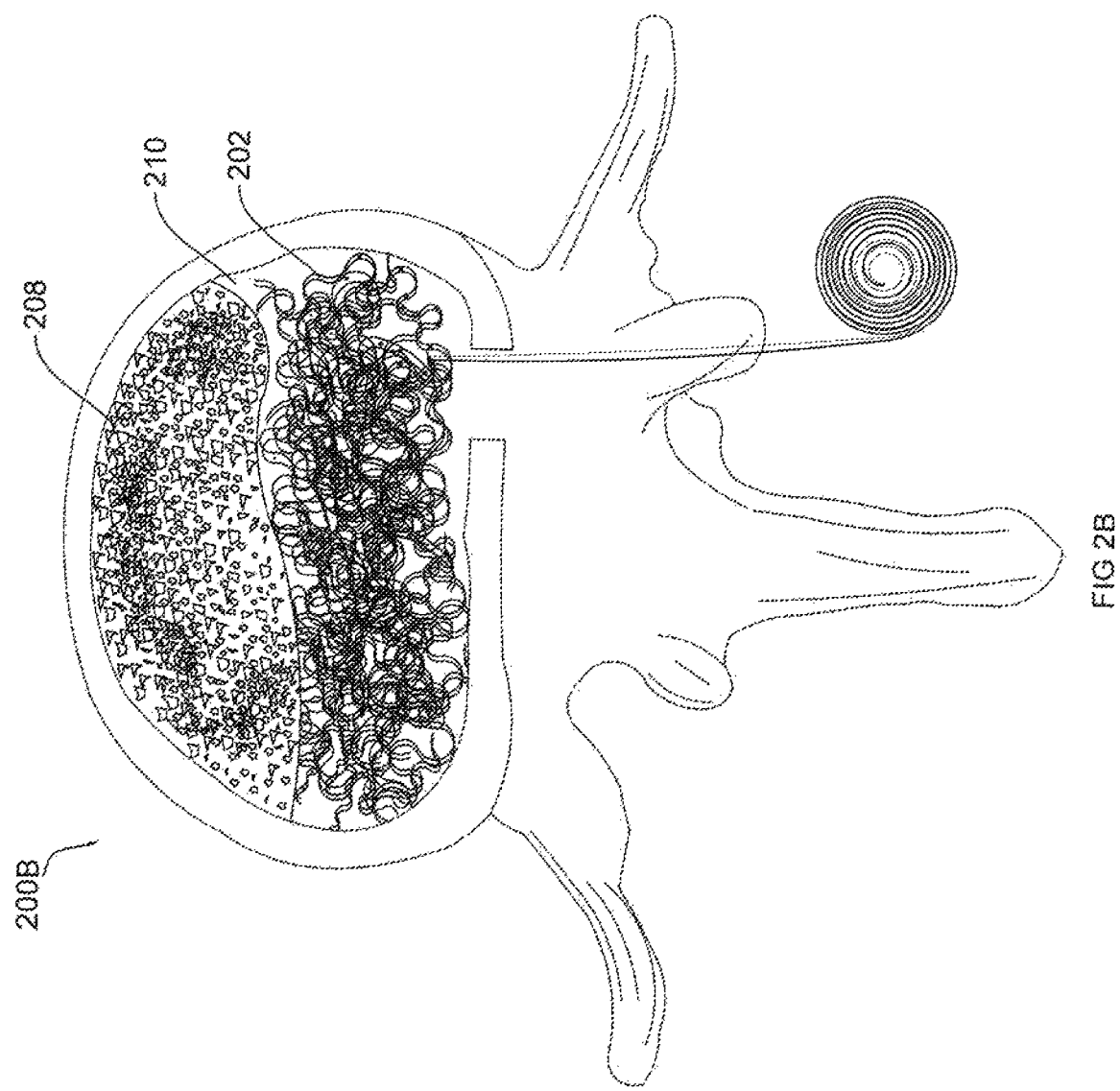

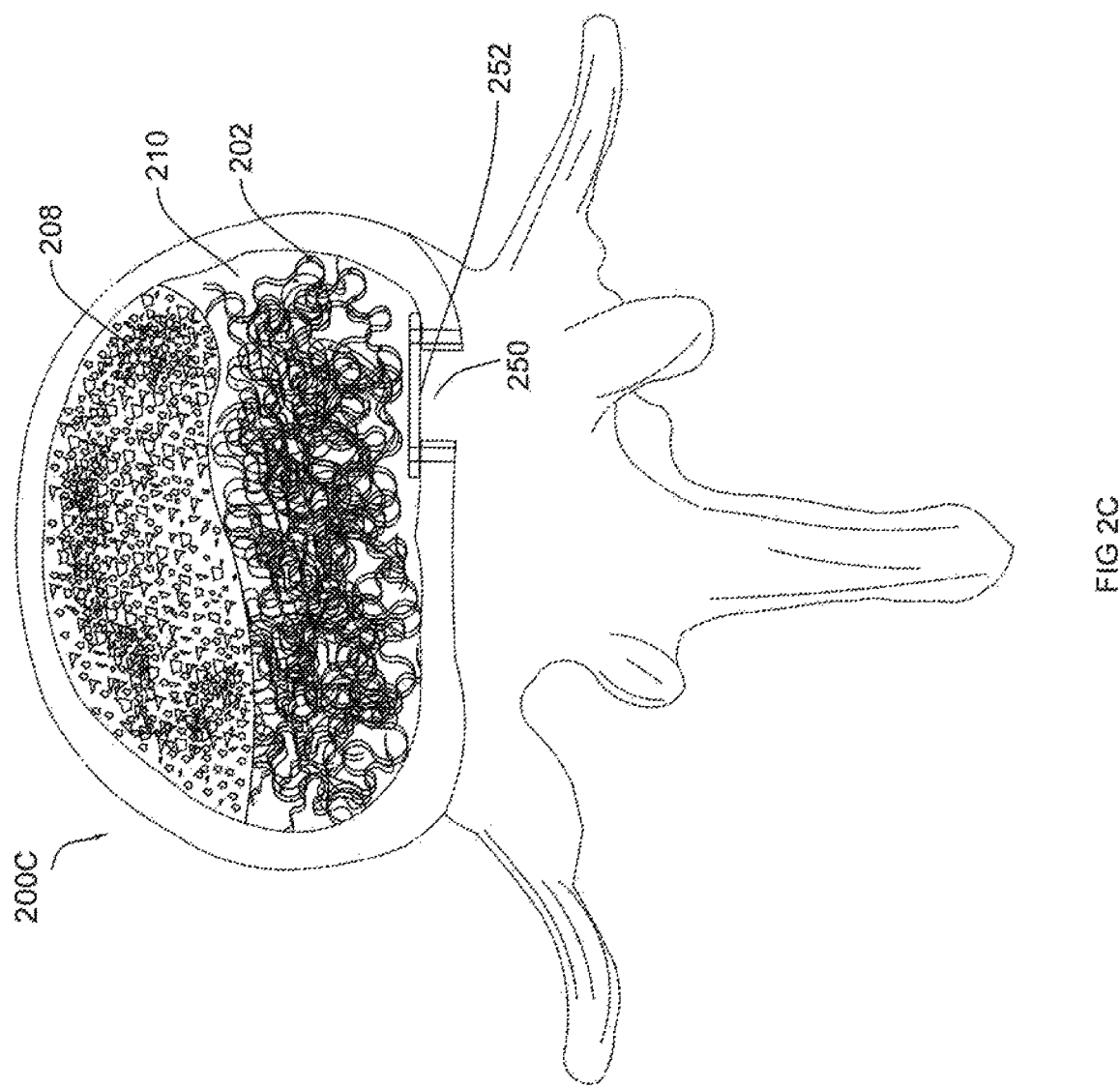

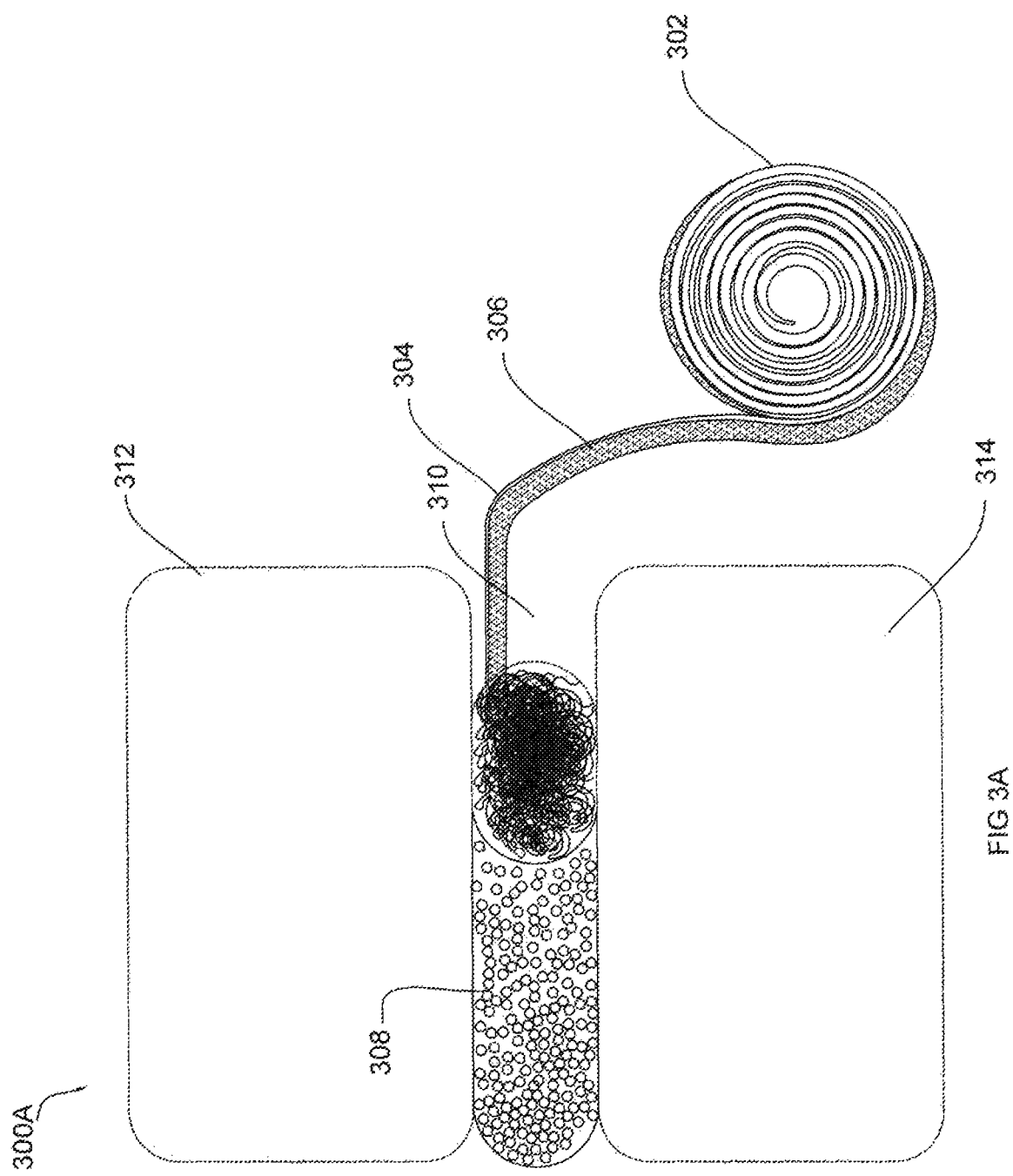

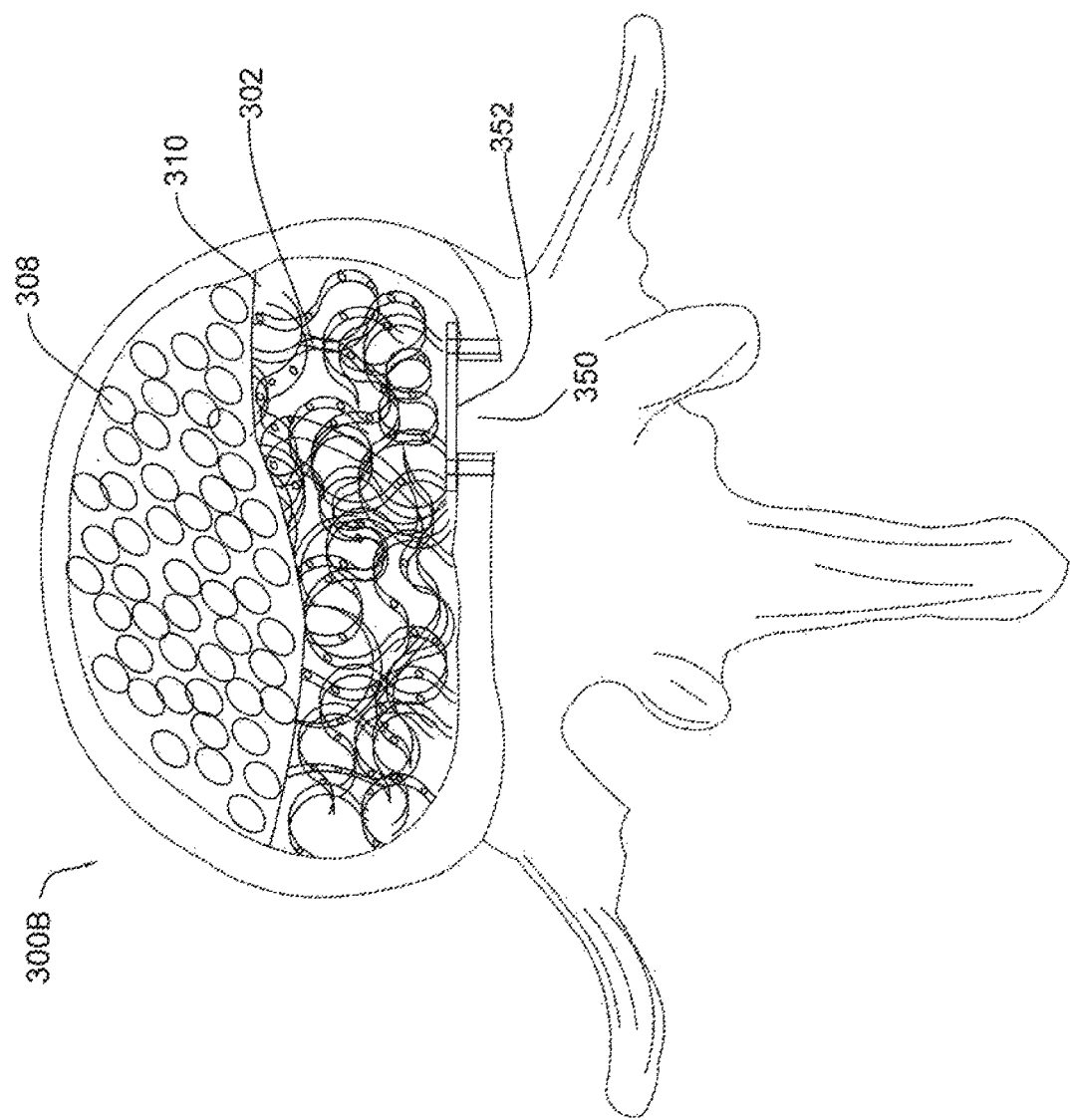

DISC AND VERTEBRAL DEFECT PACKING TAPE

CROSS-REFERENCE TO RELATED APPLICATION(S)

This application is a continuation-in-part of and claims priority to U.S. Ser. No. 15/384,301 filed on Dec. 19, 2016, entitled "Disc and Vertebral Defect Packing Tape," the contents of which are incorporated herein by reference in its entirety.

FIELD OF INVENTION

The present disclosure relates generally to field of surgery and in particular to novel materials and methods for correction of spinal defects during orthopaedic surgeries.

BACKGROUND

The background description includes information that may be useful in understanding the present invention. It is not an admission that any of the information provided herein is prior art or relevant to the presently claimed invention, or that any publication specifically or implicitly referenced is prior art.

Orthopaedic spinal defects can be either congenial or can develop later in life because of trauma or ageing causing damage/degeneration of spinal bones. They may also develop on account of bad posture. Conservative care can generally be the first option for treatment of such spinal defects. However, it may always not give the best results and intervention through corrective surgery may have to be resorted to.

Spinal surgeries typically require packing of intervertebral space for stabilizing a disc with the intention of fusing vertebras, creating an artificial disc or regeneration of the disc using stem cells or such similar materials. This may be preceded by removal of herniated/bulging disc material that may be pressing a nerve root/spinal cord or total removal of the disc. The disk will have an empty space, after partial or near total discectomy. The empty space may also result from trauma or degeneration. Similar empty space may result in the vertebral body/bone from trauma, degeneration, or surgery and all such cases require packing of empty space.

Many biocompatible and bio-absorbable materials such as collagen fibers, silk fibers, collagen gels, cements, Plaster of Paris, etc. have been developed to meet such surgical requirements. But just matching the mechanical properties especially in musculoskeletal system is not sufficient for efficient load transfer. The host tissues must successfully integrate with these materials and vascularize. Further these materials are suitable either for packing intervertebral space or empty space in vertebral body/bone. It is required to have a packing material that can be used both for process of bone implantation and also for inter vertebral disc and mimic the physiological and the biomechanical function of the replaced disc.

SUMMARY

There is a need for a device for use during spinal surgeries for packing empty intervertebral space and empty space in vertebral body/bone. The packing of intervertebral space or empty space in vertebral body/bone may be to stabilize a disc with the intention of fusing vertebras, creating an artificial disc or regeneration of the disc or to reconstruct missing portion of the bone from trauma, degeneration, or surgical excisions.

A novel packing device referred to as disc or vertebral defect packing tape ("tape") is provided that meets the above described requirements and overcomes limitations of existing packing devices. As used herein, the term "tape" means, without limitation, a disc or a bone packing/fusion/regeneration device.

According to an embodiment, the tape comprises: (1) a tape body and; (2) one or more support members. The support member can be an endoskeleton or an exosekelton. The support members can be contained within the tape body, envelope an external surface of the tape body or they can be contained within the tape body and also envelope an external of the tape body. The tape body functions as a disc packing material and the support member holds the tape body together.

The support member can be made of a soft biocompatible material such as polyethylene, nylon, silk, titanium or any other similar material. Alternatively it can be made of any suitable biologically absorbable material.

According to another embodiment, the support member comprises a plurality of metallic beads. The beads may be sized such that they are enclosed within the tape body. The beads can made of titanium or another suitable material. Each of the beads can be spaced apart from an adjacent bead by a predetermined distance. Alternately, the beads can be connected with extremely thin titanium fiber. For instance, the fiber may have the diameter of a strand of human hair. The support member can comprise one or more than one rows of these beads. In another embodiment, the support member can be configured as a single strand or as a braided wire.

The tape body comprises a biologically absorbable material. For instance, the tape body includes morselized bone, finely ground materials or a combination thereof. For example, the tape body can comprise or be impregnated with a biocompatible material, morselized allograft, finel ground materials, polyethylene, bone marrow or BMP (or any osteo-inductive or osteo-genic material), biological glue/biological cement, stem cells or other such material, and combinations thereof, and can be used for disc or bone fusing and regeneration without any other filling material. In yet another embodiment, the tape body can be of cable-type having a circular cross-section.

According to an embodiment, an impacting instrument can be configured for packing the tape tightly into the spacing between discs or within a bone defect.

In one embodiment, the tape can be used in combination with polyethylene balls for creating an artificial disc.

In one embodiment, a method of fusing a disc involves packing of empty intervertebral space and empty space in vertebral body with the tape. Each disc includes a strong outer ring of fibers called the annulus fibrosus and a soft, jelly-like center called the nucleus. After the tape is packed, a defect in the annulus may be covered/closed using a "annulus cover". The annulus cover that can comprise a square or rectangular sheet. The sheet can comprise a soft material used in the body of the tape. In an aspect, the method further involves stapling the "annular cover" in place.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 1A-FIG. 1L" illustrate exemplary views of a tape in accordance with one or more embodiments FIGS. 2A-FIG. 2C illustrate exemplary schematic representations of an empty disc space packed with a tape for disc fusion or regeneration in accordance with one or more embodiments.

FIGS. 3A-FIG. 3B illustrate exemplary schematic representations of an empty disc space packed with a tape in accordance with one or more embodiments.

DETAILED DESCRIPTION

Figure 2A:
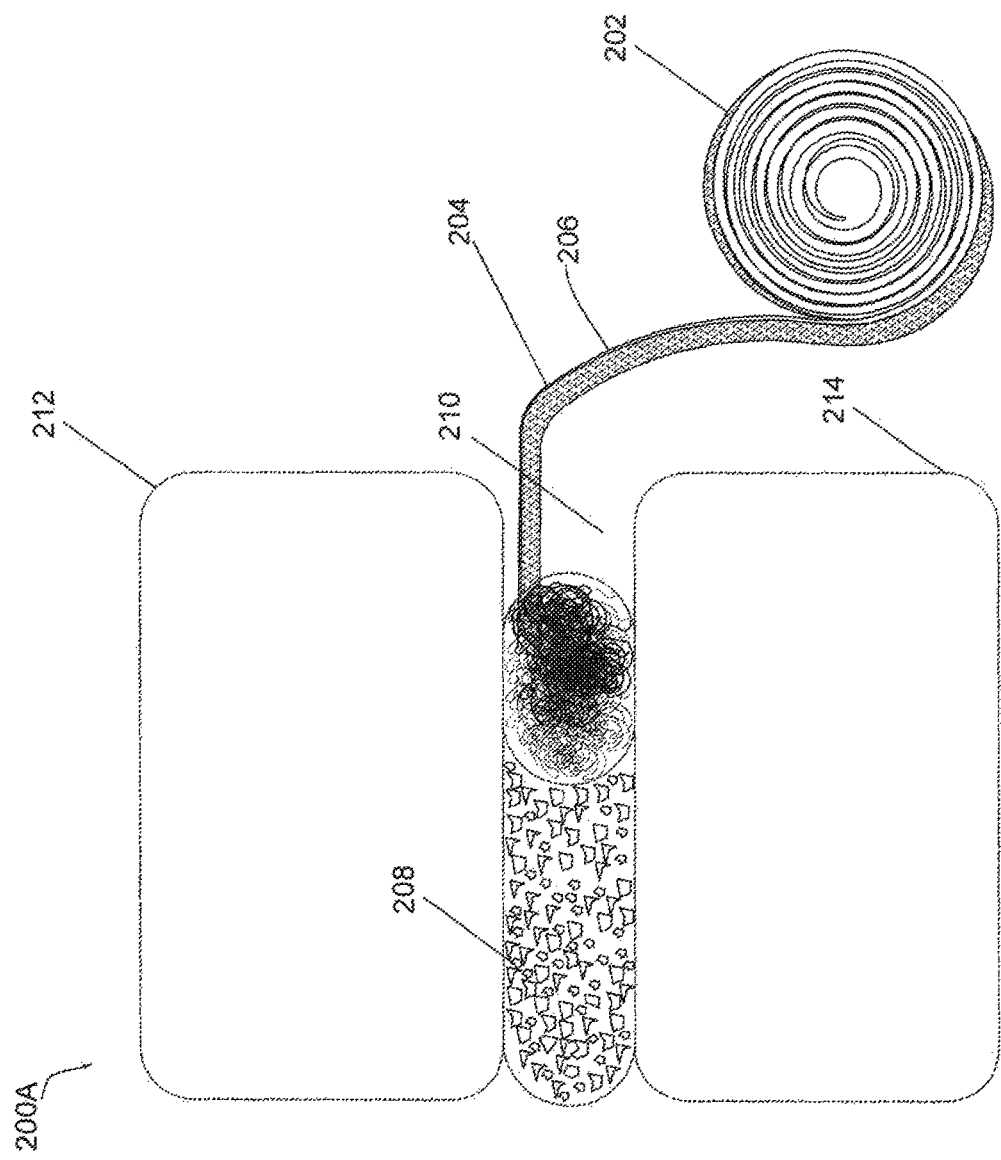

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms are used herein. To the extent a term used in a claim is not defined below, it should be given the broadest definition persons in the pertinent art have given that term as reflected in printed publications and issued patents at the time of filing.

Referring now to FIG. 1A to FIG. 1L", exemplary views of a disc and vertebral defect packing tape ("tape") are disclosed. The tape comprises a tape body and one or more support members. The tape body can be made up of biocompatible material, finely ground materials, allograft, polyethylene, etc., or a bio absorbable material and combinations thereof. The support member can be made of titanium. The support member can also be made of a soft biocompatible material such as polyethylene, nylon, silk or any other similarly suitable material, including, bio absorbable material. The tape body, depending on intended purpose, can be further impregnated with one or combination of other materials such as bone marrow or BMP (or any osteo-inductive or osteo-genic material), biological glue/biological cement, stem cell etc. Alternatively the tape body can be devoid any such impregnation. The tape body can be configured to have a plurality of different widths and thickness. Additionally, the tape body may have a greater width and thickness than the support members.

The tape body functions as a disc packing material and the support member holds the tape body together. In one more embodiments, the support member may have a relatively small diameter and its thickness may be comparable to a strand of human hair.

Referring now to FIG. 1A, the tape 100 comprises a tape body 102 and a support member 104. The tape body 102 can be a flattened strip. The support member 104 may be contained within the tape body 102.

FIG. 1B depicts another embodiment of the tape 110. As shown, the tape 110 comprises a tape body 112 and a support member 114. The support member 114 includes comprising a plurality of beaded elements 116. As shown in FIGS. 1B and 1B', the beaded elements 106 may be interconnected using a suitable connector 118. The beaded elements 116 may be arranged in a row. Each of the beaded elements may be spaced apart from an adjacent beaded element by a predetermined distance. The connector 118 can be a fiber made of titanium or a fiber made of another suitable material. Alternately, the connector 118 can be a suitable medical or biocompatible adhesive.

Another embodiment is illustrated in FIG. 1C. As shown, the tape 120 can include a tape body 122. Two support members 124A and 124B (collectively "support members 124") may be contained within the tape body 122. The support members 124 comprises a plurality of beaded elements 126. As described with reference to FIG. 1B, the beaded elements 126 may be interconnected by a connector 128.

FIG. 1D depicts yet another embodiment of tape 130. As shown, the tape 130 comprises a tape body 132. The tape body 132 may have a cylindrical or cable-type structure. A single stranded wire-like support member 134 may be enclosed within the tape body 132. The support member 134 is made of a suitable material. For example, the support member 134 comprises a single strand of titanium wire.

FIG. 1E depicts another embodiment of tape 140. As shown, the tape 140 comprises a tape body 142. The tape body 142 may have a cylindrical or cable-type structure. A braided wire-like support member 144 may be enclosed within the tape body 142. The support member 144 is made of a suitable material. For example, the support member 144 comprises a braided titanium wire.

FIG. 1F depicts another embodiment of the tape 150. As shown, the tape 150 includes a rectangular-shaped tape body 152. A single stranded wire-like support member 154 is contained within the tape body 152.

FIG. 1G depicts yet another embodiment of the tape 160. As shown, the tape 160 includes a rectangular-shaped tape body 162. A braided wire-like support member 164 is enclosed within the tape body 162.

FIG. 1H depicts yet another embodiment of tape 170. As shown, the tape 170 includes a rectangular-shaped tape body 172. A support member 174 comprising a plurality of beads 176 may be contained within the tape body 172. The beads 176 may be interconnected with a suitable connector 178 described earlier.

FIGS. 1K and 1K' depict perspective and vertical-sectional views of another embodiment of the tape 180. As shown, the tape 180 is devoid of a tape body such that the tape 180 only includes a support member 182. As shown, the support member 182 is an exoskeleton (as opposed to the endoskeleton depicted in FIGS. 1-H).

FIGS. 1L, 1L' and 1L" depict perspective, vertical-sectional and cross-sectional views of another embodiment of the tape 190. The tape 190 includes a tape body 192. The tape 190 further includes an internal support member 194A. As shown, the internal support member 194A comprises a plurality of beaded elements 196. The beaded elements 196 may be connected with a connector 198. The tape 190 further includes an exoskeleton or external support member 194B that substantially covers or envelops the internal support member 194A and the tape body 192.

It would be obvious to a person skilled in the art that the number, nature and position of the support members can be varied without deviating from the scope of the invention. For example, it may be possible to have one or more support members embedded within the tape body and one or more support members located on an external surface of the tape body. The support members may be interconnected or individual beaded elements, straight wires, braided wires, strands, etc. It is understood that each of these embodiments is encompassed within the scope of the present invention.

FIGS. 2A-2C illustrate using an embodiment of the tape, described above, for facilitating disc fusion or disc regeneration. FIG. 2A illustrates a perspective view 200A of a tape 202 packed in an empty disc space 210. The tape 202 can include a tape body 204 and a support member 206. The empty space 210 is present between two parts 212 and 214. In practice, parts 212 and 214 can be vertebrae of the spine and empty space 210 can be a void left after discectomy that may need filling for the purpose of disc fusing or disc regeneration. Alternatively, the empty space 210 can be within a vertebra body that may need packing to reconstruct missing portions of the bone due to trauma, degeneration, or surgical excision. In practice, the anterior portion of the empty space 210 may be first packed with a first substance 208. The first substance 208 may include morselized or finely ground bone, bone graft, biocompatible material like allograft or other osteo-genic, osteo-inductive or osteo-conductive material or any combination of these. The first substance 208 may also be impregnated with bone marrow or BMP or any osteo-inductive or osteo-genic materials or any other such type of materials. The tape 202 may be packed in the posterior end of the space 210 such that it abuts the first substance 208. The tape 202 can be impregnated with biological glue or biological cement. Such a procedure can be adopted when intended purpose is disc fusion or regeneration.

FIG. 2B is a top view 200B of the embodiment shown in FIG. 2A. As shown, tape 202 is packed in space 210 such that it abuts a first substance 208. FIG. 2C is a top view 200C of another embodiment wherein, after the empty space 210 is packed with the first substance 208 and the tape 202, the opening in the annulus 250 is closed by stapling a plate or a polyethylene or similar membrane 252 known in the art.

In another embodiment (not shown), the tape 202 can be used to reconstruct missing portion of the bone from trauma, degeneration, or surgical excision. The procedure shall be same as followed for disc fusion. The empty space caused by the missing bone can be treated like an empty disk space and packed using morselized bone preferably auto-graft and thereafter tape 202 made of bio absorbable material and impregnated with bone marrow can be packed.

FIGS. 3A-3B illustrate creation of an artificial disk using an embodiment of the tape described earlier. FIG. 3A illustrates a perspective view 300A of a tape 302 packed in an empty disc space 310. The tape 302 can include a tape body 304 and a support member 306. The empty space 310 is present between two parts 312 and 314. In practice, parts 312 and 314 can be vertebrae of the spine and empty space 310 can be a void left after discectomy that may need filling for artificial disc formation. The anterior portion of the space 310 may be filled with a second substance 308. The second substance 308 may include any suitable matter, such as, polyethylene balls 308. In practice, the anterior portion of the empty space 310 may be first filled with polyethylene balls 308, and thereafter the posterior of empty space 310 can be packed with tape 302. The tape 302 can be impregnated with biological glue or biological cement. Such a procedure can be adopted when intended purpose is creation of an artificial disc.

FIG. 3B is a top view 300B of another embodiment wherein, after the empty space 310 is packed with the second substance 308 and the tape 302, an opening in the annulus 350 is closed stapling a plate or a polyethylene or similar membrane 352 known in the art.

Figure 4:
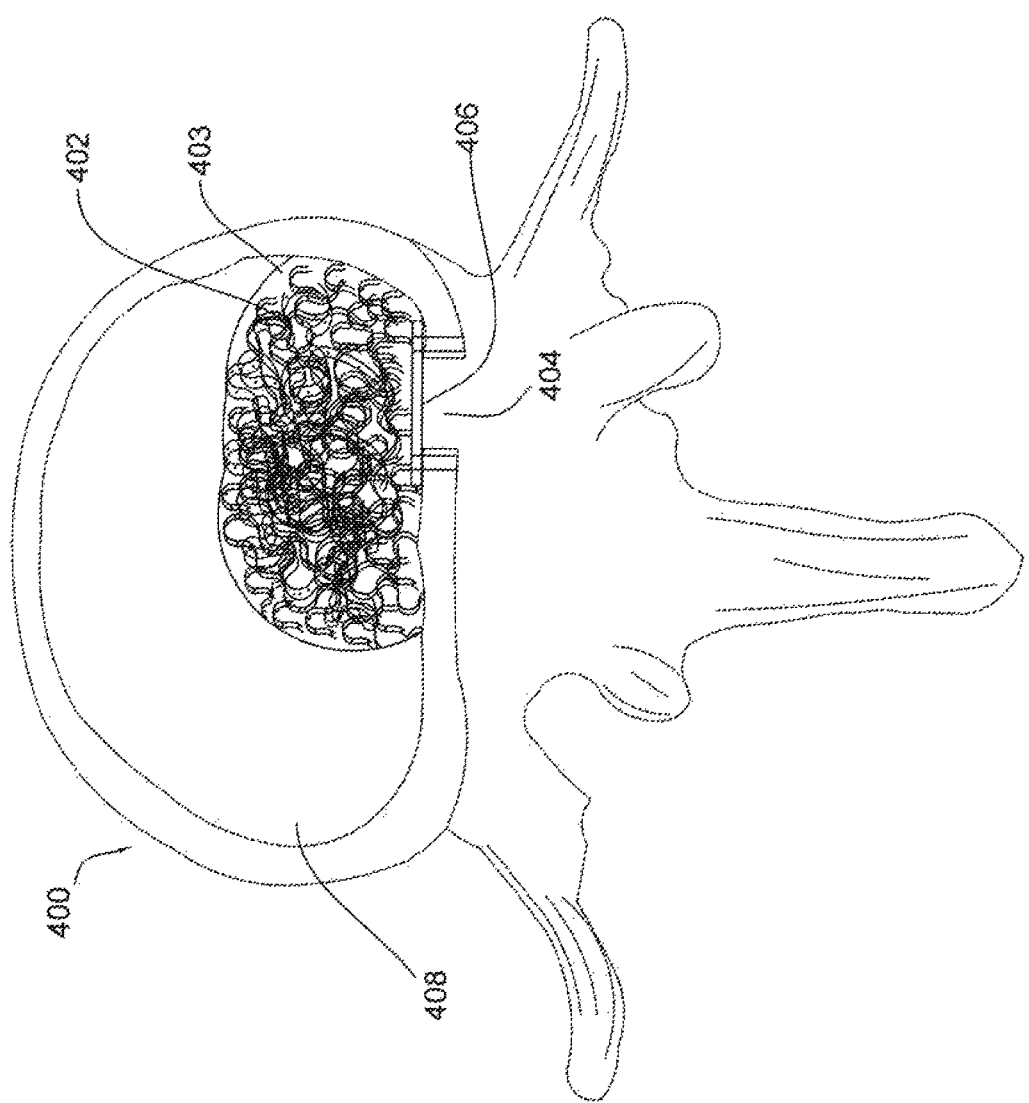
FIG. 4 illustrates an exemplary schematic representation of an empty disc space packed with a tape in accordance with one or more embodiments.

FIG. 4 illustrates a top view 400 of disk 408 having an empty disk space 403. When the intended purpose is regeneration of the disk, the disk removal can be minimal to ensure that all the potentially healthy disk material remains intact. The limited empty space in the disk 408 can then be packed with tape 402 made of bio absorbable material, incorporating stem cells or other tissues capable of regenerating the disk 408. Thereafter, the opening in the annulus 404 can be closed by stapling a plate or a polyethylene or similar membrane 406 known in the art.

Figure 5:
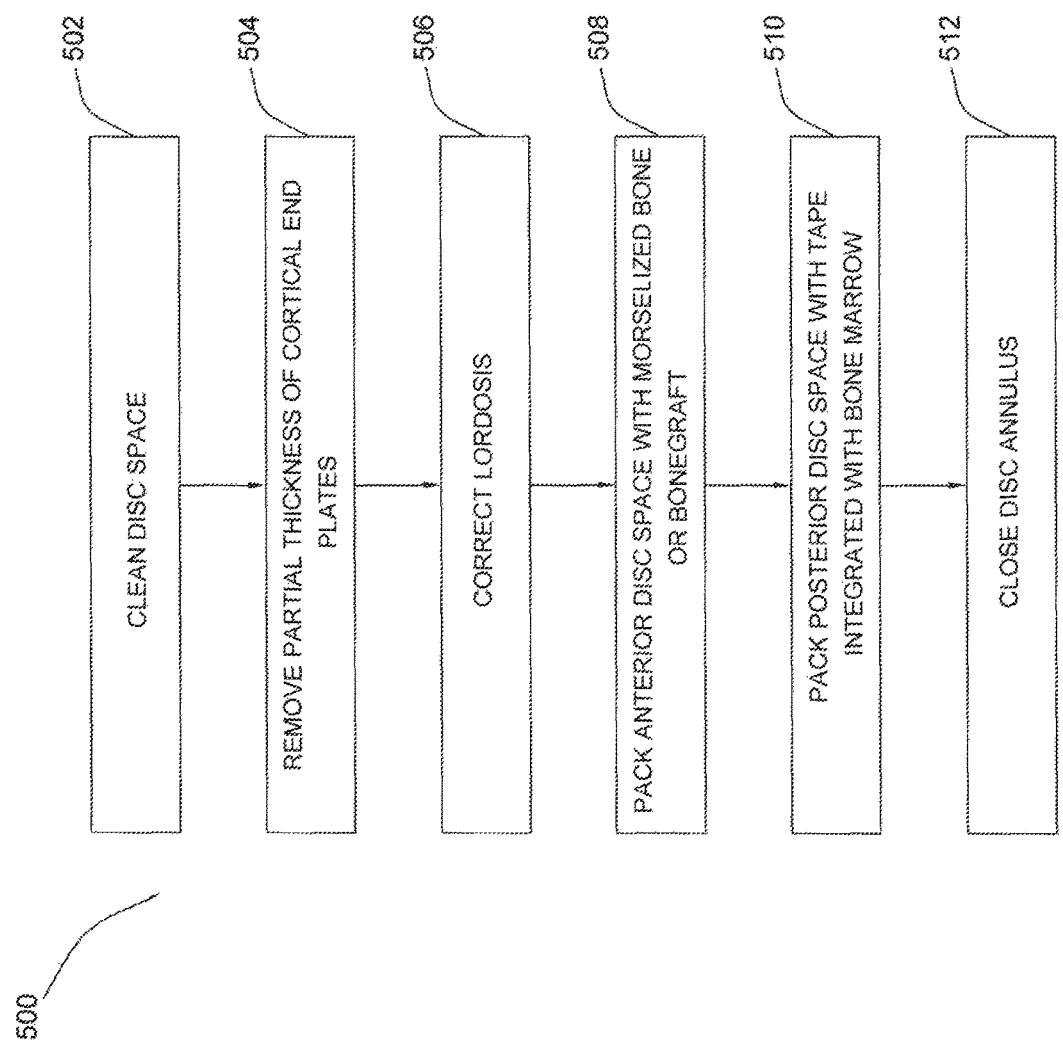
FIG. 5 illustrates an exemplary process flow diagram for disc fusion using the tape in accordance with an embodiment.

FIG. 5 illustrates an exemplary method flow diagram 500 for disc fusion using the tape. At step 502 of the process, the disk space can be thoroughly cleaned out. At step 504, partial thickness of the cortical end plates can be removed by scraping with a suitable device, such as, a curette. At step 506, a desired lordosis for that particular disc can be created, using a specialized instrument. (An exemplary instrument for creating the lordosis is described below with reference to FIGS. 8A and 8B). At step 508, an anterior portion, for example, an anterior two-third of the disk space can be packed with a first substance, such as, morselized bone, preferably autograft. At step 510, the remainder posterior portion, for example, the remaining one-third disk space can be packed with a tape made of a bio compatible material and may be impregnated with bone marrow, BMP, or other osteo-inductive and osteo-genic material. At step 512, on completion of the packing, a square or rectangular piece of polyethylene or similar membrane or a plate, can be stapled to close the disk annulus that can facilitate containment of the tape mass inside the disk space. The membrane can be of same material as used for the body of the tape.

Figure 6:
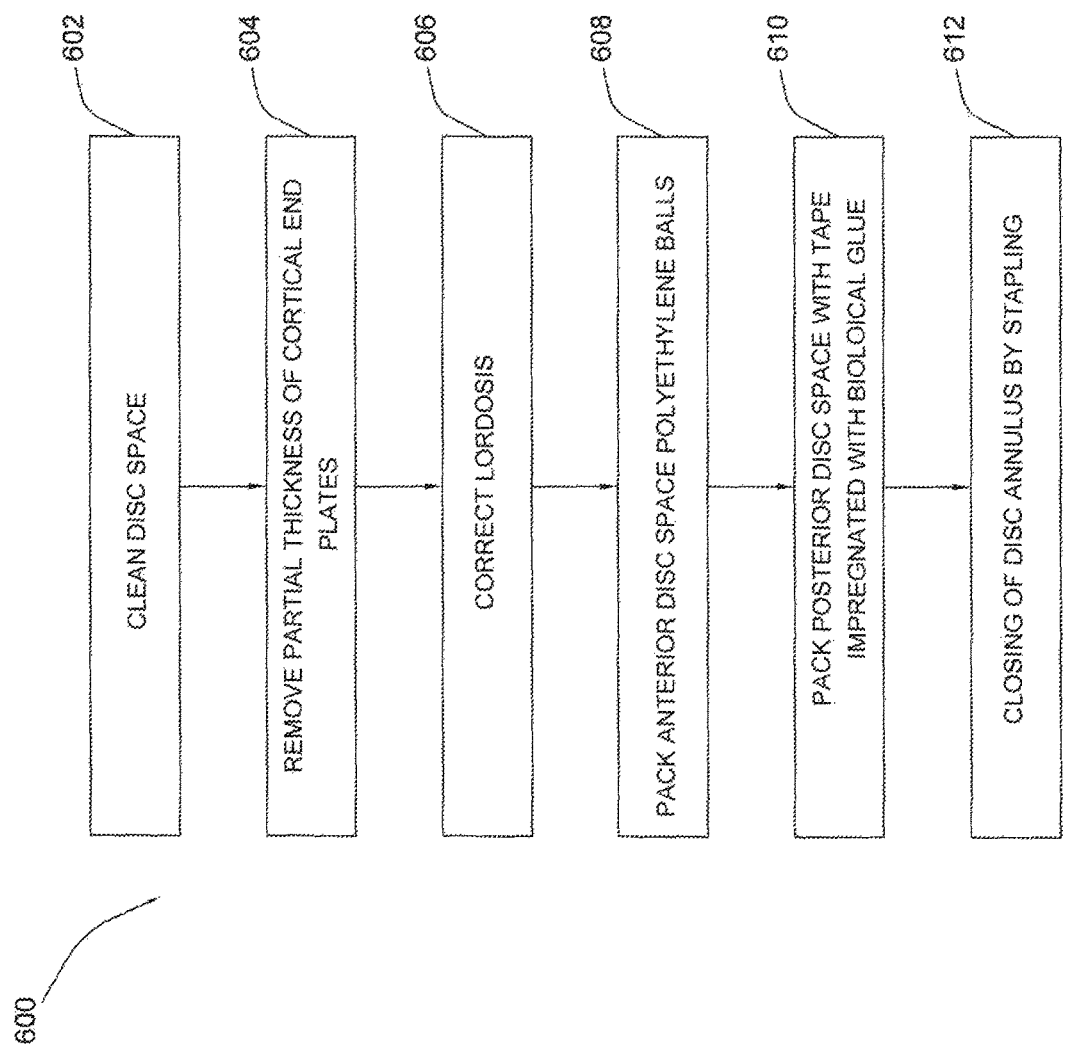
FIG. 6 illustrates an exemplary process flow diagram for creating an artificial disc using the tape in accordance with an embodiment.

FIG. 6 illustrates an exemplary process flow diagram 600 for creating an artificial disc using the tape in accordance with an embodiment. As shown, at step 602, the disk space can be thoroughly cleaned out. At step 604, a partial thickness of the cortical end plates can be removed by scraping with a suitable device, such as, a curette. At step 606, using a special instrument, a desired lordosis for that particular disk can be created. At step 608, an anterior portion, for example, a two-third of the disk space can be packed with a second substance, such as, polyethylene or similar balls. At step 610, the remainder posterior portion, for example, the remaining one-third disk space can be packed with a tape made of a bio compatible material and impregnated with appropriate biological glue or polyethylene or similar material that can help to convert the packed tape into one single mass, trapped in the disk space and behaving like an artificial disk. On completion of packing and at step 612, a square or rectangular piece of polyethylene or similar membrane or a plate can be stapled to close the disk annulus in order to facilitate containment of the tape mass inside the disk space. The membrane can be of same material as used for the tape.

Figure 7:
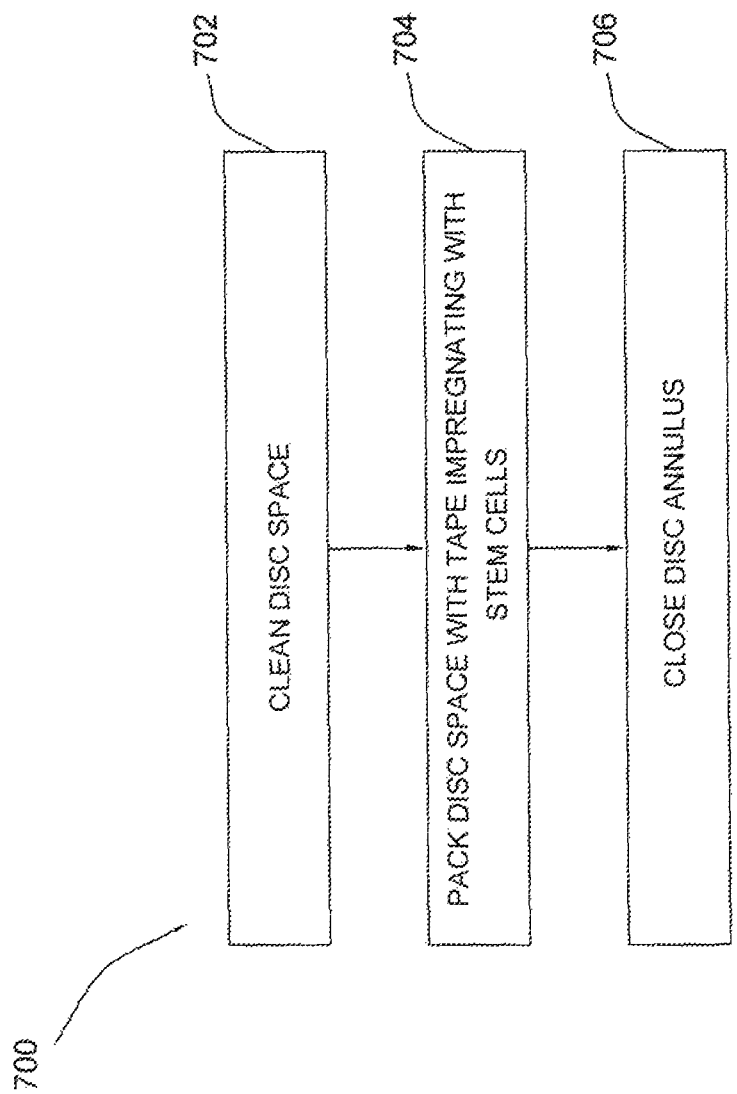
FIG. 7 illustrates an exemplary process flow diagram for disc regeneration using the tape in accordance with an embodiment.

FIG. 7 illustrates an exemplary process flow diagram 700 for disc regeneration using the tape in accordance with an embodiment. When the intended purpose is regeneration of the disk, the disk removal to clean disc space at step 702 can be minimal to ensure that all the potentially healthy disk material remains intact. At step 704, the empty space in the disk can then be packed with the tape. The tape can incorporate stem cells or other tissues capable of regenerating the disk. Thereafter, at step 706 the opening in the annulus can be closed by stapling a polyethylene or similar membrane or a suitable plate.

According to an embodiment, the tape can be tightly packed in an empty disk space manually or by using a specialized impacting instrument (not shown).

Figure 8A:
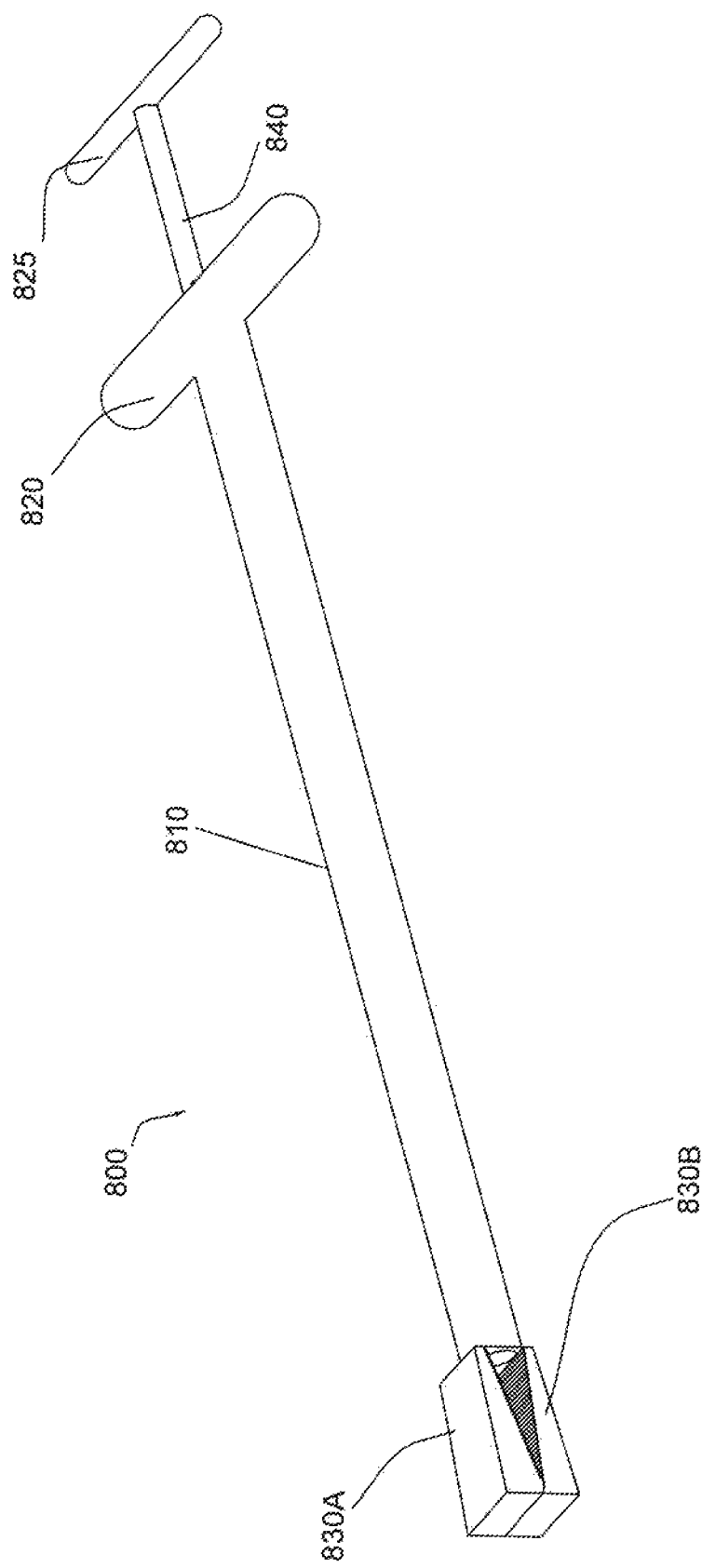
FIGS. 8A and 8B illustrate an exemplary instrument for creating lordosis in accordance with an embodiment.
Figure 8B:
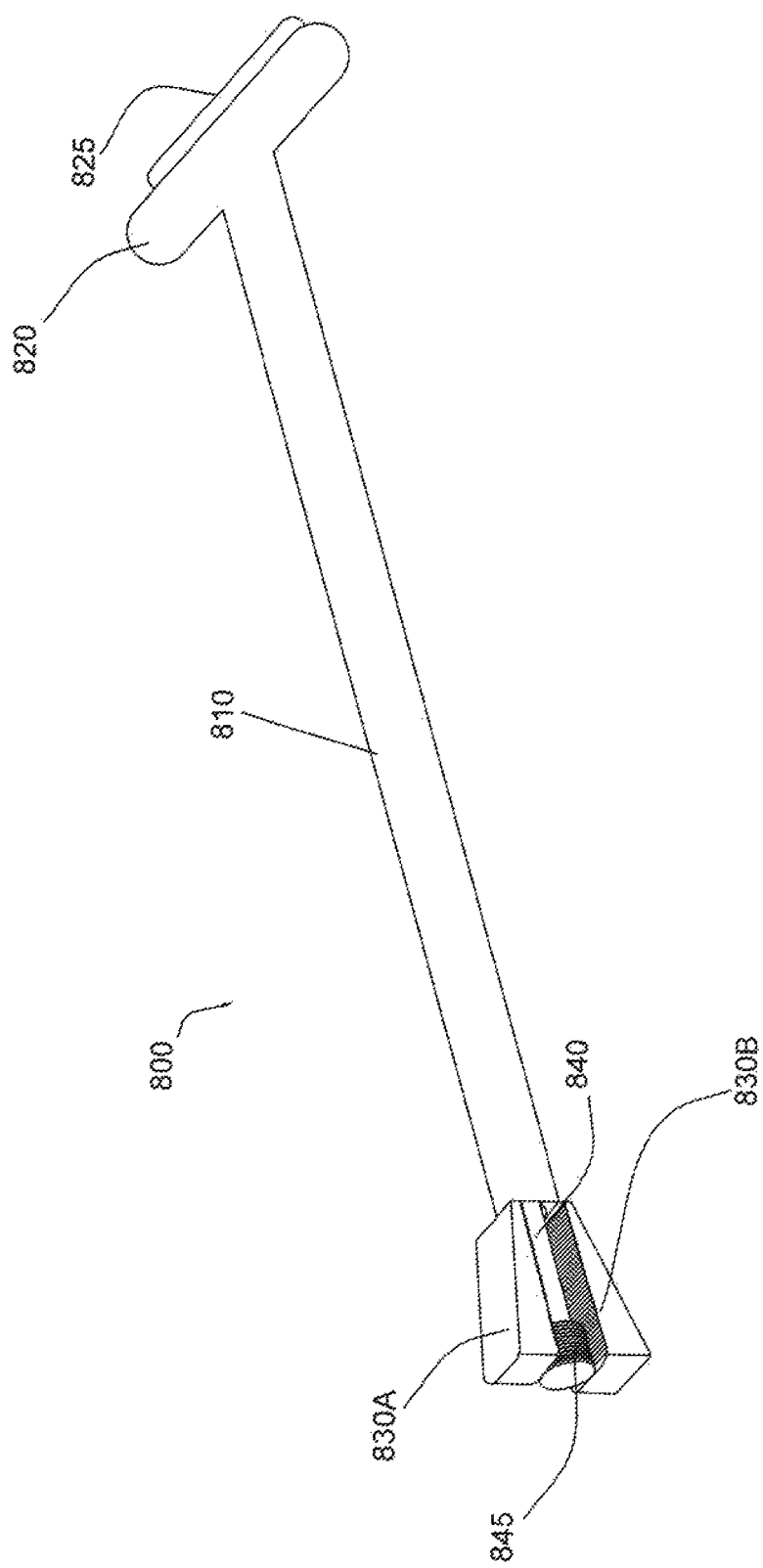

FIGS. 8A and 8B illustrate an exemplary instrument 800 for creating a desired lordosis. FIG. 8A illustrates a lordosis disk spreader 800. The lordosis disk spreader 800 includes an elongated cylindrical body 810. A pair of upper and lower wedged-shaped members 830A, 830B are formed at a front end of body 810. A distal end of the body 810 includes a first handle 820. An elongate cylindrical column 840 is inserted within the body. The column 840 terminates in a second handle 825. As illustrated in FIG. 8B, the lordosis disk spreader 800 can be actuated by pushing the second handle 825 toward the first handle 820. This causes the column 840 to be propelled within the body 810 such that a front end of the column 845 extends out between the wedge-shaped members 830A, 830B thereby creating the desired lordosis.

Thus, the embodiments of the tape can be used during spinal surgeries for packing empty intervertebral space and empty space in vertebral body/bone with an intention of fusing vertebrae, creating an artificial disc, helping regeneration of the disc, or to reconstruct missing portion of disc or bone from trauma, degeneration, or surgical excisions.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

The invention claimed is:

1. A method for disc regeneration comprising:
cleaning a disc space to create an empty space, wherein cleaning the disc space further comprises the step of: removing a minimal amount of disc material such that healthy disc material remains intact;
packing the empty space in the disc with a disc or vertebral defect packing tape, the tape comprising:
one tape body; and
one or more support members for holding the tape body together, wherein the one or more support members are:
(A) contained within the tape body as an internal support member, wherein the tape body is wider than the internal support member; and/or
(B) substantially enveloping an external surface of the tape body as an external support member, wherein the external support member comprises a fine mesh of biocompatible material, wherein the tape body is configured as a packing material for packing an empty intervertebral disc space, and wherein the tape body is selected from a group consisting of a biologically absorbable material, stem cells, finely ground materials, or a combination thereof; and
closing an opening in an annulus of the disc.

2. The method according to claim 1, wherein the tape is impregnated with stem cells or other materials capable of facilitating disk regeneration.

3. The method according to claim 1, wherein the internal and external support members comprise a biocompatible material and/or a biologically absorbable material.

4. The method according to claim 1, wherein the internal support member comprises a plurality of beaded elements.

5. The method according to claim 4, wherein the beaded elements comprise titanium beads.

6. The method according to claim 5, wherein the beads are interconnected with titanium fiber.

* * * * *